US008211822B2

(12) United States Patent
Mueller et al.

(10) Patent No.: US 8,211,822 B2
(45) Date of Patent: Jul. 3, 2012

(54) METHOD FOR PRODUCING PROPYLENE OXIDE

(75) Inventors: Ulrich Mueller, Neustadt (DE); Georg Krug, Moerlenbach (DE); Peter Rudolf, Ladenburg (DE); Joaquim Henrique Teles, Otterstadt (DE); Hans-Georg Goebbel, Kallstadt (DE); Peter Bassler, Viernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 260 days.

(21) Appl. No.: 12/556,961

(22) Filed: Sep. 10, 2009

(65) Prior Publication Data

US 2010/0003173 A1 Jan. 7, 2010

Related U.S. Application Data

(62) Division of application No. 10/555,961, filed as application No. PCT/EP2004/004971 on May 10, 2004, now Pat. No. 7,608,728.

(30) Foreign Application Priority Data

May 8, 2003 (DE) .................. 103 20 635

(51) Int. Cl.
*B01J 21/06* (2006.01)
*B01J 21/08* (2006.01)
(52) U.S. Cl. ....................................... 502/242
(58) Field of Classification Search .................. 502/242
See application file for complete search history.

(56) References Cited

U.S. PATENT DOCUMENTS

| | | | |
|---|---|---|---|
| 3,393,156 A | 7/1968 | Hansford | |
| 6,008,389 A | 12/1999 | Grosch et al. | |
| 6,066,750 A | 5/2000 | Chang | |
| 6,479,680 B1 * | 11/2002 | Bassler et al. | 549/529 |
| 6,491,861 B1 | 12/2002 | Grosch et al. | |
| 2004/0192945 A1 | 9/2004 | Teles et al. | |

FOREIGN PATENT DOCUMENTS

| | | |
|---|---|---|
| CA | 2 390 875 | 5/2001 |
| CN | 1266382 | 9/2000 |
| DE | 198 35 907 | 2/2000 |
| DE | 199 39 416 | 2/2001 |
| DE | 102 32 406 | 1/2004 |
| EP | 0 200 260 | 12/1986 |
| EP | 0 311 983 | 4/1989 |
| EP | 0 389 041 | 9/1990 |
| EP | 0 405 978 | 1/1991 |
| EP | 0 883 439 | 6/2001 |
| WO | 95/19222 | 7/1995 |
| WO | 98/55228 | 12/1998 |
| WO | WO 98/55229 | * 12/1998 |
| WO | 02/28774 | 4/2002 |
| WO | 03/008401 | 1/2003 |

OTHER PUBLICATIONS

Wu et al., "A Novel Titanosilicate with MWW Structure", Journal of Catalysis, 202, pp. 245-255 (2001).
Wu et al., "Extremely High Trans Selectivity of Ti-MWW in Epoxidation of Alkenes with Hydrogen Peroxide", The Royal Society of Chemistry, No. 10, pp. 897-898 (2001).
Wu et al., "Hydrothermal Synthesis of a Novel Titanosilicate with MWW Topology", Chemistry Letters, pp. 774-775 (2000).
Meier et al., "Atlas of Zeolite Structure Types", $5^{th}$ Ed., pp. 202-203 (2001).
"Fiscal Year 2001, Report on the results of developing next-generation chemical process technology and of developing non-halogen chemical process technology", Japan Chemical Inovation Institute, Mar. 2002 (with English translation).
"Ninth Symposium on the Development of Next-generation Chemical Process Technology—Development of Non-halogen Chemical Process Technology—, Mar. 2003, Japan Chemical Inovation Institute", Mar. 6, 2003 (with English Translation).
Chinese Office Action issued May 12, 2010, in Chinese Patent Application No. 200910151697.1 (w/English translation).
Chinese Office Action issued Dec. 6, 2011, in Chinese Patent Application No. 20091015169/.1 (w/English translation).

* cited by examiner

*Primary Examiner* — Bernard Dentz
(74) *Attorney, Agent, or Firm* — Oblon, Spivak, McClelland, Maier & Neustadt, L.L.P.

(57) ABSTRACT

Process for preparing propylene oxide, which comprises at least the steps (i) and (ii):

(i) providing a catalyst comprising at least one porous oxidic material;

(ii) reacting propene with a hydroperoxide in at least one nitrile as solvent or in a solvent mixture comprising at least one nitrile in the presence of the catalyst of (i), wherein the at least one porous oxidic material is a zeolite which is assigned X-ray-crystallographically to the MWW type.

8 Claims, No Drawings

METHOD FOR PRODUCING PROPYLENE OXIDE

The present invention relates to a process for preparing propylene oxide, in which propene is reacted with a hydroperoxide in a solvent which either is a nitrile or comprises a nitrile. This reaction is catalyzed by a zeolite catalyst of the X-ray-crystallographic structure type MWW. The present invention relates quite generally to the use of a zeolite catalyst of the X-ray-crystallographic structure type MWW for the epoxidation of propene by means of a hydroperoxide.

The epoxidation of olefins using hydroperoxides in the presence of a catalyst and at least one solvent is dealt with in many documents of the prior art.

Thus, for example, WO 02/28774 A2 describes a process in which a zeolite catalyst of the structure type MWW is used for the epoxidation of a compound having a C—C double bond. Here, the to be reacted must have not only the C—C double bond but also, mandatorily, at least one further functional group. As further functional groups, a series of further groups including halogen, aldehyde, ketone, ester, amide or amine groups are disclosed. In the catalytic processes of WO 02/28774 A2, only the porous material of the zeolite is used; shaped catalyst bodies, however, are not produced from the porous material.

In "Hydrothermal Synthesis of a novel Titanosilicate with MWW Topology", Chemistry Letters 2000, pp. 774-775, Wu et al. describe the preparation of a novel titanium silicalite having an MWW structure. This silicalite is prepared directly using boron as structure-forming agent. The titanium-containing MWW zeolite prepared in this way is tested for its catalytic activity in the liquid-phase oxidation of alkenes. These catalytic tests are carried out using only the porous material of the zeolite; shaped catalyst bodies, however, are not produced from the porous material. The only alkene which is explicitly disclosed by Wu et al. as being oxidized by means of the MWW zeolite is cyclohexene. Wu et al. describe cyclohexene as part of a series including toluene, which was disproportionated by means of MWW zeolite catalysis, and benzene, which was alkylated by means of MWW zeolite catalysis. When using this MWW active material in the reaction of cyclohexene with hydrogen peroxide, selectivities to the undesirable downstream products of the glycols of at least 28% are accepted, in the reaction with tert-butyl hydroperoxide still at least 4%.

It is an object of the present invention to provide a process by means of which an alkene can be reacted so that the selectivity to the undesirable glycol reaction downstream products is less than that described in the prior art.

Therefore, the present invention relates to a process for preparing propylene oxide, which comprises at least the steps (i) and (ii):

(i) providing a catalyst comprising at least one porous oxidic material;
(ii) reacting propene with a hydroperoxide in at least one nitrile as solvent or in a solvent mixture comprising at least one nitrile in the presence of the catalyst of (i), wherein the at least one porous oxidic material is a zeolite which is assigned X-ray-crystallographically to the MWW type.

In the process of the present invention, the conversion of hydroperoxide with which propene is reacted is at least 90%.

Based on hydroperoxide, the selectivity to the process product propylene oxide in the process of the present invention is at least 80%, preferably at least 85% and particularly preferably at least 88%.

Based on the starting material hydroperoxide, the selectivity to the epoxide reaction downstream products formed in the process of the present invention is not more than 10%, more preferably not more than 8%, even more preferably not more than 6% and particularly preferably not more than 5%.

Accordingly, the present invention also relates to a process as described above in which the selectivity to the epoxide downstream products is not more than 10%, based on hydroperoxide.

The term "epoxide downstream product" as used in the context of the present invention refers to all conceivable downstream products which can be formed from the propylene oxide formed during the reaction (ii) in the reactor in which the reaction of propene with the starting hydroperoxide is carried out. These are, in particular, glycols such as propylene glycol and polyether polyols and/or hydroperoxides which are formed from the propylene oxide formed and the hydroperoxide used, for example hydrogen peroxide.

The selectivity to the glycol downstream products from the group of epoxide downstream products is not more than 5%, preferably not more than 4%, more preferably not more than 3% and particularly preferably not more than 2%.

The catalyst which is provided in (i) and used for the reaction in (ii) comprises a porous oxidic material which in turn is a zeolite of a particular structural type. Zeolites are, as is known, crystalline aluminosilicates having ordered channel and cage structures and having, for example, micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher "Atlas of Zeolite Structure Types", Elsevier, 5$^{th}$ edition, Amsterdam 2001.

Zeolites which contain no aluminum and in which the Si(IV) in the silicate lattice is partly replaced by titanium as Ti(IV) are likewise known. These titanium zeolites, in particular those having a crystal structure of the MWW type, and possible ways of preparing them are described, for example, in the above-cited WO 02/28774 A2 or in the above-cited article by Wu et al, the respective content of which is incorporated into the context of the present invention by reference. For example, specific syntheses of Ti-MWW are described in examples 1 to 5 of WO 02/28774 A2.

Apart from silicon and titanium, such materials can further comprise additional elements such as aluminum, zirconium, tin, iron, cobalt, nickel, gallium, germanium, boron or small amounts of fluorine. In the titanium zeolite catalysts which are preferably used in the process of the present invention, the titanium of the zeolite can be partly or completely replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.001:1 to 0.1:1.

It is known that titanium zeolites having an MWW structure can be identified via a particular X-ray diffraction pattern and also via a lattice vibration band in the infrared region (IR) at 960±5 cm$^{-1}$, and in this way differ from alkali metal titanates or crystalline and amorphous $TiO_2$ phases such as rutile, anatase or brookite.

In general, all of the above-described zeolites of the MWW structure type can be used in the process of the present invention. Preference is given to using titanium zeolites.

Accordingly, the present invention also relates to a process as described above in which the zeolite of the MWW type is a titanium zeolite.

In particularly preferred embodiments, the titanium zeolite of the MWW type which is used in the process of the present invention has the following chemical composition (I) or (II):

$$x \cdot TiO_2 (1-x) \cdot SiO_2 \quad (I)$$

where $0.0001 \leq x \leq 0.2$, or

$$x \cdot TiO_2 \cdot y \cdot M_2O_3 (1-x-2y) \cdot SiO_2 \quad (II)$$

where $0.0001 \leq x \leq 0.2$ and $0.0001 \leq y \leq 0.1$ and M is at least one element from the group consisting of aluminum, boron, chromium, gallium, germanium and iron. The variables x and y are the respective mole fractions.

Further details regarding the structure type MWW may be found in the abovementioned reference by W. M. Meier, D. H. Olson and Ch. Baerlocher "Atlas of Zeolite Structure Types", Elsevier, 5$^{th}$ edition, pages 202 and 203, Amsterdam, 2001, the respective content of which is incorporated in the present application by reference.

In the process of the present invention, it is also possible to use titanium zeolite catalysts comprising either at least two of the titanium zeolites of the composition (I) or at least two of the titanium zeolites of the composition (II) or at least one titanium zeolite of the composition (I) and at least one titanium zeolite of the composition (II).

The porous oxidic material can in principle be used as such as catalyst in the process of the present invention. The preparation of the porous oxidic material is subject to essentially no restrictions, as long as a zeolite and preferably a titanium zeolite of the structure type MWW is obtained. With regard to the synthesis of the porous oxidic material, reference may be made, for example, to the above-cited WO 02/28774 A2 and Wu et al., the relevant contents of which are hereby fully incorporated by reference into the present patent application.

In a particularly preferred embodiment of the process of the present invention, the titanium zeolite of the type MWW prepared, for example, as in WO 02/28774 A2 is separated off from its mother liquor by a suitable method and, more preferably, is dried by one or more suitable methods and once again preferably is subsequently calcined. The calcination is preferably carried out, for example, in a suitable gas atmosphere, particularly preferably using air and/or lean air as gas atmosphere.

All methods of separating the titanium zeolite from its mother liquor are conceivable. They include, for example, filtration, ultrafiltration, diafiltration and centrifugation methods or, for instance, spray drying processes and spray granulation processes. The titanium zeolite is preferably separated off from the mother liquid by spray drying or by ultrafiltration. Before separating the zeolite from the mother liquor, it is possible to increase the zeolite content of the mother liquor by concentrating. It is likewise possible to employ exclusively one or more concentration processes instead of the separation of the zeolite from the mother liquor. Details regarding the separation of the zeolite from the mother liquor may also be found in DE 102 32 406.9, which is hereby fully incorporated by reference into the disclosure of the present patent application.

If further drying is desired, for example after spray drying, the titanium zeolite which has been separated off from the mother liquor is dried at generally from 80 to 160° C., preferably from 90 to 145° C. and particularly preferably from 100 to 130° C. The calcination which preferably occurs subsequently is generally carried out at from 400 to 750° C., preferably from 450 to 600° C. and particularly preferably from 490 to 530° C.

In further embodiments of the process of the present invention, the zeolite can, after it has been separated off from the mother liquor, be brought into contact with a water-containing composition. This contacting can likewise be carried out for the first time or repeated after the above-described drying procedure and/or the above-described calcination. In these cases, one or more of the above-described treatments for concentration or for separation can follow the contacting with the water-containing composition. As water-containing composition, preference is given, for example to water itself. It is likewise possible to use aqueous amine solution, in which the amine or amines present can be ammonia, an organic aliphatic amine or a quaternary ammonium hydroxide, where the nitrogen in these nitrogen compounds can bear, for example, methyl, ethyl or propyl radicals as alkyl radicals and two or more different alkyl radicals may also be bound to one nitrogen. The contacting with, for example preferably, water itself generally takes place at from room temperature to 750° C., preferably from 100 to 250° C. and particularly preferably from 120 to 175° C., wherein contacting preferably lasts for a period of from 12 to 48 hours. This contacting very particularly preferably takes place in an autoclave.

If the zeolite has been dried and/or calcined after being separated off from the mother liquor and has subsequently been brought into contact with a water-containing composition, another drying and/or calcination step can follow. This drying is generally carried out at from 80 to 160° C., preferably from 90 to 145° C. and particularly preferably from 100 to 130° C. The subsequent calcination which preferably occurs is generally carried out at from 400 to 750° C., preferably from 450 to 600° C., and particularly preferably from 490 to 530° C.

In addition to or instead of contacting with the water-containing composition, the zeolite can be washed with, for example, hydrogen peroxide solution, preferably sulfuric hydrogen peroxide solution. It is likewise possible to treat the zeolitic material with alkali metal ions to convert the zeolite from the H form into the cationic form.

If the zeolite is, according to the preferred embodiment, brought into contact with the water-containing composition after being separated off from the mother liquor, the zeolitic material obtained has, when used in the process of the present invention, the advantage over untreated zeolites that the selectivity of the reaction to the undesirable by-product oxygen, based on hydroperoxide, is significantly reduced. While the oxygen selectivity in the case of an untreated zeolite is generally in the range from 11 to 15%, the contacting with the water-containing composition which is preferred according to the present invention can reduce the oxygen selectivity to not more than 10%, preferably not more than 9%, more preferably not more than 8% and particularly preferably not more than 7%. The other parameters of interest, for example hydroperoxide conversion, selectivity to the epoxide downstream products and the propylene oxide selectivity remain within the abovementioned preferred ranges.

The porous oxidic material of the titanium zeolite can generally be used as such as catalyst for the epoxidation, as is also described in the abovementioned WO 02/28774 A2 for the reaction of olefins having at least one further functional group or in the likewise abovementioned article by Wu et al. in the case of the reaction of cyclohexene.

In a preferred embodiment of the process of the present invention, the porous oxidic material, viz. the active component of the zeolite catalyst, is not used as catalyst directly after calcination but instead shaped catalyst bodies are produced from the porous oxidic material in an additional processing step.

Accordingly, the present invention also relates to a process as described above in which the production of the catalyst provided in (i) comprises at least the steps (a) and (b):
(a) preparing the at least one porous oxidic material;
(b) producing a shaped body using the porous oxidic material obtained in (a).

The shaped catalyst bodies can in general be produced by all suitable methods. As regards the specific step of production of a shaped body, reference may be made to WO 98/55229 and DE 102 32 406.9, whose relevant contents are incorporated by reference into the context of the present patent application.

Preference is given to admixing the zeolitic material which has been separated off from the mother liquor and, if appropriate, subjected to at least one of the abovementioned further treatments, e.g. washing, drying, calcination, contacting with a water-containing composition or treatment with hydrogen peroxide solution, with at least one binder. Further additives such as mixtures of water and at least one alcohol or at least one viscosity-increasing organic compound or at least one pore-forming compound, as are known from the prior art, can likewise be added.

As binder, it is in principle possible to use any compound which increases the cohesion between the particles of the zeolitic material. Preferred binders are binders selected from the group consisting of hydrated silica gel, silicic acid, silica gel, tetraalkoxysilicates, tetraalkoxytitanates, tetraalkoxyzirconates and mixtures of two or more thereof. Particular preference is given to tetramethoxysilicate, tetraethoxysilicate, tetrapropoxysilicate, tetrabutoxysilicate or silica sol. Particular preference is given to tetramethoxysilicate, tetraethoxysilicate and silica sol, with silica sol being very particularly preferred.

Further binders are described in WO 98/55229 and DE 102 32 406.9, whose relevant contents are incorporated by reference into the context of the present patent application.

The binders mentioned can be used either alone or as mixtures of two or more thereof. Further binders such as oxides of silicon, boron, phosphorus, zirconium and/or titanium can be used in addition.

The production of the shaped body according to the present invention is generally carried out using up to 80% by weight, preferably from 10 to 75% by weight and particularly preferably from 20 to 40% by weight, of binder, based on the total weight of the shaped body.

In a further preferred embodiment of the process of the present invention, at least one pore former is added to the zeolitic material. Preference is in this case given to using polymers, more preferably polymers which can be dispersed, emulsified or suspended in water or aqueous solvents. This polymer or these polymers is/are preferably selected from the group consisting of vinyl polymers such as polystyrene, polyacrylates, polymethacrylates, polyolefins, polyamides and polyesters. After production of the shaped bodies, these pore-forming polymers are removed from the shaped body by calcination at appropriate temperatures. If polymers are added as pore formers, they are added in a proportion of generally from 5 to 50% by weight, preferably from 7 to 35% by weight and particularly preferably from 10 to 20% by weight, in each case based on the total weight of the inorganic components of binder and zeolite.

Further preference is given to adding at least one extrusion aid. As extrusion aid, it is possible to use essentially any compound which leads to an improvement in the mixing, kneading or flow properties. Preference is given to organic hydrophilic polymers such as cellulose, cellulose derivatives, for example alkylcelluloses, starch, polyacrylates, polymethacrylates, polyvinyl alcohol, polyvinylpyrrolidone, polyisobutene or polytetrahydrofuran. According to the present invention, these compounds are used, also because they increase the mechanical stability of the shaped bodies, preferably during shaping and drying and during subsequent use as shaped catalyst bodies. These compounds are removed from the shaped body by calcination at appropriate temperatures.

Further additives are described in EP 0 389 041 A, EP 0 200 260 A and WO 95/192222, whose relevant contents are incorporated by reference into the context of the present patent application.

In a preferred embodiment of the process of the present invention, the addition of the binder or binders to the zeolitic material is followed by addition of at least one organic viscosity-increasing compound and homogenization of the resulting composition in a kneading apparatus or extruder for from 10 to 180 minutes. This homogenization is carried out at temperatures which are generally about 10° C. below the boiling point of the extrusion aid. The pressure employed is generally approximately ambient pressure or slightly superatmospheric pressure.

In a further preferred embodiment of the process of the present invention, firstly the pore-forming compound or compounds and subsequently the binder or binders are added to the zeolitic material during the kneading procedure. After these have been added, the water-containing composition or compositions, preferably water, is/are added in one or more steps. In a further preferred embodiment, firstly the pore-forming compound or compounds and subsequently part of the binder or binders are added during kneading, and part of the water-containing composition or compositions, preferably water, is/are then added in one or more steps. The remainder of the binder is then added, followed by the remainder of the water-containing composition or compositions, preferably water, in one or more steps.

Preference is given to adding silica sol and/or a polystyrene dispersion and/or cellulose and/or a cellulose derivative such as an alkylcellulose and/or polyethylene oxide and/or water to the zeolitic material. For example, the zeolitic material is preferably admixed with silica sol, a polystyrene dispersion, methylcellulose and water and then homogenized by kneading in a suitable apparatus.

Accordingly, the present invention also describes a process as described above in which the production of the shaped body in (b) comprises at least the step (aa):
(aa) kneading the porous oxidic material obtained in (a) with addition of at least one binder or at least one extrusion aid or at least one pore former or a water-containing composition or a mixture of two or more thereof.

In a more preferred embodiment, the composition which has been kneaded as described above is shaped to produce a shaped body. This can generally be carried out by any suitable methods. In the process of the present invention, the shaped bodies are preferably produced by means of an extruder. Preference is given to producing extrudates having a diameter in the range from 1 to 10 mm, more preferably from 1 to 5 mm and particularly preferably from 1 to 2 mm.

Shaping can be carried out at ambient pressure or at a pressure above ambient pressure, generally a pressure in the range from 1 to 700 bar. Furthermore, shaping can be carried out at ambient temperature or at a temperature higher than ambient temperature, generally at a temperature in the range from 20 to 300° C. Shaping can also be carried out in a controlled atmosphere, generally an inert gas atmosphere, a reducing atmosphere or an oxidizing atmosphere.

The individual shaped bodies can in general be separated off from the strand of molding composition leaving the extruder by all possible methods. The paste-like strand of molding composition in the extruder is particularly preferably separated off by bringing the paste-like molding composition into contact with at least one stream comprising at least one fluid medium to divide it. The fluid medium is more preferably a gas or a liquid, particularly preferably essentially air. Preference is likewise given to the strand of the paste-like molding composition being divided periodically. This method makes it possible to produce shaped bodies which have a higher bulk density than is obtained by the mechanical separation methods of the prior art. This is particularly advantageous when the shaped bodies are used in fixed-bed reactors.

Accordingly, the present invention also describes a process as described above in which the production of the shaped body in (b) comprises at least the steps (aa) and (bb):
(aa) kneading the porous oxidic material obtained in (a) with addition of at least one binder or at least one extrusion aid or at least one pore former or a water-containing composition or a mixture of two or more thereof;
(bb) shaping the kneaded mixture obtained in (aa) to give at least one shaped body.

The present invention therefore also relates quite generally to a shaped catalyst body comprising at least a porous oxidic material as catalytically active material, wherein the porous oxidic material is a zeolite which can be assigned X-ray-crystallographically to the MWW type.

Apart from the zeolite which can be assigned X-ray-crystallographically to the MWW type, the shaped body of the present invention can further comprise, for example, at least one of the above-described additives which can be used in production of the shaped body.

The shaped bodies are then preferably dried at from 30 to 140° C., preferably from 60 to 135° C. and particularly preferably from 90 to 130° C., with the drying times generally being in the range from 1 to 20 h, preferably from 2 to 10 h and particularly preferably from 3 to 5 h. The heating rates employed are generally from 0.5 to 5° C./min, preferably from 1 to 4° C./min and particularly preferably from 1.5 to 3° C./min.

Accordingly, the present invention also describes a process as described above in which the production of the shaped body in (b) comprises at least the steps (aa) to (cc):
(aa) kneading the porous oxidic material obtained in (a) with addition of at least one binder or at least one extrusion aid or at least one pore former or a water-containing composition or a mixture of two or more thereof;
(bb) shaping the kneaded mixture obtained in (aa) to give at least one shaped body;
(cc) drying the shaped body obtained in (bb).

The dried shaped bodies are then preferably calcined at from 400 to 800° C., preferably from 425 to 600° C. and particularly preferably from 450 to 500° C., with the calcination times generally being in the range from 1 to 20 h, preferably from 2 to 10 h and particularly preferably from 3 to 7 h. The heating rates employed are generally from 0.25 to 2° C./min, preferably from 0.5 to 1.5° C./min and particularly preferably from 0.75 to 1.25° C./min. Very particular preference is given to calcining the dried shaped body under air and/or lean air.

Accordingly, the present invention also describes a process as described above in which the production of the shaped body in (b) comprises at least the steps (aa) to (dd):
(aa) kneading the porous oxidic material obtained in (a) with addition of at least one binder or at least one extrusion aid or at least one pore former or a water-containing composition or a mixture of two or more thereof;
(bb) shaping the kneaded mixture obtained in (aa) to give at least one shaped body;
(cc) drying the shaped body obtained in (bb);
(dd) calcining the dried shaped body obtained in (cc).

Accordingly, the present invention also describes a shaped catalyst body as described above which is obtainable by a process comprising the step (aa) or the steps (aa) and (bb) or the steps (aa), (bb) and (cc) or the steps (aa), (bb), (cc) and (dd).

Before or after the drying and/or calcination of the shaped bodies obtained in (bb), they can, as described above with regard to the zeolitic material, be brought into contact with a water-containing composition. If the dried and/or calcined shaped bodies ire brought into contact with the water-containing composition, this is preferably followed by another drying and/or calcination step which is/are carried out as described under (cc) and/or (dd).

Accordingly, the present invention also provides a shaped catalyst body as described above which is obtainable by a process comprising the step (aa) or the steps (aa) and (bb) or the steps (aa), (bb) and (cc) or the steps (aa), (bb), (cc) and (dd), wherein the shaped body is brought into contact with a water-containing composition after step (bb) or step (cc) or step (dd).

The process of the present invention preferably gives shaped bodies which have pores whose volumes are generally in the range from 0.5 to 2.0 ml/g, preferably in the range from 0.7 to 1.4 ml/g and particularly preferably in the range from 0.9 to 1.3 ml/g. The pore volumes are in the present context the values determined by mercury porosimetry in accordance with DIN 66133.

In the shaped bodies preferably obtained, the diameter of about 80% of the pores is in the range from 4 nm to 1 µm. The pores have a bimodal distribution in which the maximum of the pore diameter is about 60 nm and the minimum is about 20 nm.

In preferred shaped bodies in the form of extrudates having a diameter of 1.5 mm, the lateral compressive strength, determined using a hardness measuring instrument from Zwick, Ulm, model Z2.5/TS1S at a preliminary advance rate of 10 mm/min and a test advance rate of 1.6 mm/min, is in the range from 2 to 9 N. Details of this apparatus may be found in the "Technisches Handbuch 441801".

Accordingly, the present invention also describes a process as described above in which the diameter of 80% of the bimodally distributed pores of the shaped body is in the range from 4 nm to 1 µm.

The present invention therefore likewise relates to a shaped body as described above in which the diameter of 80% of the bimodally distributed pores of the shaped body is in the range from 4 nm to 1 µm.

In the process of the present invention, at least one hydroperoxide is reacted with the propene. For the purposes of the present patent application, the term "hydroperoxide" refers to a compound of the formula ROOH. Details regarding the preparation of hydroperoxides and regarding hydroperoxides which can be used, inter alia, in the process of the present invention may be found in DE 198 35 907 A, whose relevant contents are incorporated by reference into the context of the present patent application. Examples of hydroperoxides which can be used for the purposes of the present invention are, inter alia, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethylnaphthalene hydroperoxide, peracids such as peracetic acid, or hydrogen peroxide. Mixtures of two or more hydroperoxides can also be used according to the present invention. Preference is given to using hydrogen peroxide as hydroperoxide in the process of the present invention, and further preference is given to using an aqueous hydrogen peroxide solution.

Accordingly, the present invention also describes a process as described above in which the hydroperoxide is hydrogen peroxide.

The solvent used according to the present invention for the conversion of propene into propylene oxide is at least one nitrile or a solvent mixture comprising at least one nitrile. Examples of such nitriles are acetonitrile, propionitrile and benzonitrile.

If a solvent mixture comprising at least one nitrile is used in the process of the present invention, any solvents suitable for the conversion of propene into propylene oxide can be used in addition to the nitrile or nitriles. Examples which may be mentioned are:

water;
alcohols, preferably alcohols having less than 6 carbon atoms, for example methanol, ethanol, propanols, butanols and pentanols;
diols or polyols, preferably those having less than 6 carbon atoms;
esters such as methyl acetate or butyrolactone;
amides such as dimethylformamide, dimethylacetamide or N-methyl-pyrrolidone;
ketones such as acetone;
mixtures of two or more of the aforementioned compounds.

Particular preference is given to using acetonitrile or a mixture of water and acetonitrile as solvent for the purposes of the present invention.

Accordingly, the present invention also describes a process as described above in which the at least one nitrile is acetonitrile.

The present invention likewise describes a process as described above in which the solvent mixture comprising at least one nitrile is a mixture of water and acetonitrile.

The present invention therefore also relates to a process as described above in which the hydroperoxide is hydrogen peroxide and the at least one nitrile is acetonitrile.

The reaction in (ii) can in general be carried out in any appropriate way. Thus, for example, it can be carried out in a batch reactor or in at least one continuously operated reactor. Particularly, when using the above-described shaped catalyst bodies, the continuous mode of operation is preferred.

Accordingly, the present invention also describes a process as described above in which the reaction in (ii) is carried out in at least one continuously operated reactor.

In a preferred embodiment, the reaction is carried out in a single continuously operated reactor. In this embodiment, the reaction is preferably carried out at from 20 to 80° C., more preferably from 25 to 70° C. and particularly preferably from 30 to 65° C. The pressures in the reactor in this case are in the range from 15 to 45 bar, preferably from 20 to 40 bar and particularly preferably from 25 to 35 bar. In particularly preferred embodiments of the process of the present invention, the reaction is carried out at temperatures and pressures at which the reaction mixture is liquid and consists of a single phase.

Accordingly, the present invention also describes a process as described above in which the reaction (ii) is carried out at from 20 to 80° C. and pressures in the range from 15 to 45 bar.

The present invention therefore also relates to a process as described above in which the reaction in (ii) is carried out in at least one continuously operated reactor at from 20 to 80° C. and pressures in the range from 15 to 45 bar.

The operating life of the catalyst in the reactor is generally at least 24 hours, preferably in the range up to 200 hours, more preferably in the range up to 500 hours and particularly preferably in the range up to 1000 hours.

After the reaction, the catalyst used in the process can be regenerated by one or more suitable methods either in the reactor or outside the reactor or both in the reactor and outside the reactor. In a preferred process, the catalyst is regenerated by means of a thermal treatment of the catalyst in the presence of a gas stream at above 120° C., preferably above 350° C. and in particular at from 400° C. to 650° C., in the reactor in which the reaction of the propene takes place. During the thermal treatment, the mass-based residence time of the gas stream over the catalyst is more than 2 hours, preferably in the range from 3 to 10 hours and particularly preferably in the range from 4 to 6 hours. The regeneration gas generally contains less than 20% by volume, preferably from 0.1 to 10% by volume, in particular from 0.1 to 5% by volume and more preferably from 0.1 to 2% by volume, of oxygen. Preference is given to using a mixture of air and respective volumes of nitrogen. The term "mass-based residence time" used for the purposes of the present invention refers to the ratio of the catalyst mass ($M_{cat}$) divided by the mass flow ($M_{gases}$) of the gas used in the regeneration. In general, the regeneration is carried out so that the pressure drop over the reactor is not more than 4 bar, preferably not more than 3 bar and in particular not more than 2.5 bar.

In a likewise preferred embodiment of the process of the present invention, the reaction of the propene can be carried out in two or more stages. A two-stage reaction takes place, for example, as follows:

(A) propene is reacted with a hydroperoxide, preferably hydrogen peroxide, in at least one nitrile as solvent or in a solvent mixture comprising at least one nitrile in the presence of the catalyst as provided in (i) to give a mixture comprising propylene oxide and unreacted hydroperoxide, preferably unreacted hydrogen peroxide;

(B) the unreacted hydroperoxide, preferably hydrogen peroxide, is separated off from the mixture resulting from (A);

(C) the hydroperoxide, preferably hydrogen peroxide, which has been separated off from (B) is reacted with propene.

It is likewise possible to have more than two reaction stages and more than one separation stage. With regard to a multi-stage reaction, reference may be made to DE 198 35 907 A, which is hereby incorporated by reference into the disclosure of the present patent application.

The reaction is in this case preferably carried out in four, more preferably three and particularly preferably two, stages with a separation stage in between, as described above. The reactions in (A) and (C) are very particularly preferably each carried out in a fixed-bed reactor, particularly preferably a fixed-bed tube reactor. In particular, the reaction in (A) is carried out in an isothermal fixed-bed reactor and the reaction in (C) is carried out in an adiabatic fixed-bed reactor.

In this embodiment, the reaction in (A) is preferably carried out at from 20 to 80° C., more preferably from 25 to 70° C. and particularly preferably from 30 to 65° C. The pressures employed in the reactor are in the range from 15 to 45 bar, preferably from 20 to 40 bar and particularly preferably from 25 to 35 bar.

The reaction in (C) is preferably carried out at from 20 to 80° C., more preferably from 25 to 70° C. and particularly preferably from 30 to 65° C. The pressures employed in the reactor are in this case in the range from 15 to 45 bar, preferably from 20 to 40 bar and particularly preferably from 25 to 35 bar.

The hydroperoxide used can be separated off in (B) by any suitable methods. The hydrogen peroxide which is preferably used is preferably separated off by distillation using one or more distillation columns, preferably one distillation column.

If two or more reactors are used for the reaction, the reactors are preferably operated so that a hydroperoxide conversion in the region of 85-95% is obtained in the first reactor and the remaining conversion is achieved in the further reactor or reactors.

The catalyst used in the respective reactor can be regenerated as described above, and the catalyst of one reactor can be regenerated in the same way as or in a different way from the catalyst of another reactor.

In a further embodiment of the process of the present invention, the reaction of the propane with the hydroperoxide can also be carried out in one or more reactors as described above, with at least one of the reactors being operated in the suspension mode.

The present invention relates quite generally to the use of a titanium zeolite which can be assigned X-ray-crystallographically to the MWW type for the epoxidation of propene with a hydroperoxide, especially to the use as catalyst for the epoxidation of propene with a hydroperoxide, preferably with hydrogen peroxide.

The present invention further provides for the use of a titanium zeolite which can be assigned X-ray-crystallographically to the MWW type for the epoxidation of propene by means of hydrogen peroxide in acetonitrile as solvent.

The process of the present invention can also be carried out in at least one reactor using at least two different zeolite catalysts of which at least two are used physically separately from one another. At least one of the zeolite catalysts is a zeolite catalyst, preferably a titanium zeolite catalyst, of the crystal structure type MWW. As described above, the zeolite catalysts can be used as zeolitic material itself or as shaped bodies, and there can be differences between the zeolite materials or between the shaped bodies.

Differences in respect of the zeolitic materials are, for example,
    the titanium content of the zeolitic material;
    the content of chemical elements other than titanium;
    the porosity of the zeolite, with the porosity being able to differ, for example, in terms of the geometry of the pores of the different zeolite catalysts and these accordingly being able to have, for example, differing pore volumes, differing pore diameters or differing surface areas of the pores; the zeolites can likewise differ in respect of the pore distribution;
    the crystal structure of the zeolitic material;
    the surface modification of the zeolitic material;
    the acidity of the zeolitic material.

Differences in respect of the shaped bodies are, for example,
    the geometry of the shaped catalyst bodies;
    the porosity of the shaped bodies;
    the mechanical strength of the shaped bodies;
    the binder content of the shaped catalyst bodies;
    the type of binder material used for producing the shaped catalyst bodies;
    the content of catalytically active zeolitic material in the shaped catalyst bodies;
    the carbon content of the shaped bodies.

For the purposes of the present invention, the term "different zeolite catalysts" also encompasses two catalyst mixtures which differ from one another and which can each comprise at least two different shaped bodies or at least two different zeolitic materials as such or at least one shaped body and at least one zeolitic material as such. Different catalyst mixtures are thus mixtures as described above which differ in terms of
    either at least one of the distinguishing features described above by way of example for zeolitic material or the shaped bodies,
    or the mixing ratio of the components present in the mixture
    or both one of the distinguishing features described above by way of example for the zeolitic material or the shaped bodies and the mixing ratio of the components present in the mixture.

The term "physically separately" as used for the purposes of the present invention refers to embodiments in which the apparatus in which the reaction is carried out has at least two compartments of which one contains a zeolite catalyst and at least one other compartment contains at least one further zeolite catalyst which differs from the zeolite catalyst present in the first compartment.

Such compartmentalization can, for example, be realized in a single reactor, with various embodiments of the compartmentalization once again being possible.

In a particularly preferred embodiment, this compartmentalization is achieved, for example by means of a structured bed of different catalysts. A first zone of the reactor is in this case provided by a bed of a first zeolitic catalyst which represents the first catalyst compartment. A second zone of the reactor is subsequently produced by pouring the second zeolitic catalyst, which differs from the first, onto the first compartment to form a second compartment. Likewise, a third compartment or further compartments can be added, with one of the first two catalysts or a zeolite catalyst which is different from the first two catalysts being able to be used in the third compartment or a further compartment. This way of producing catalyst zones is referred to as "a structured bed" for the purposes of the present invention.

Compared to conventional processes in which a reactor is equipped with only a single zeolite catalyst, this structured bed offers the advantage that targeted selection of the catalysts used in various reactor zones enables, for example, the conversion in the reaction to be influenced in a positive way. For example, in a continuous process in which the reactants propene and hydroperoxide are conveyed through the reactor and pass through the various reactor zones provided with the different zeolite catalysts, the individual catalysts can be matched to the progress of the reaction.

It is thus possible, for example, to choose the zeolite catalyst in a first zone of the reactor in which the concentration of unreacted reactants is high in such a way that the conversion, for example in an exothermic reaction, is just so high that the heat evolved can still be removed. In a next reactor zone in which the concentration of the reactants is lower, it is then possible to use a zeolite catalyst which achieves, for example, a higher conversion, i.e. is more active in respect of the reaction. The inhomogeneity in the concentrations of the reactants hydroperoxide and propene as they pass through the reactor and the resulting inhomogeneity in the reaction mixture comprising the reactants hydroperoxide and propene and the reaction product or products formed therefrom can accordingly be compensated by appropriate selection of different zeolite catalysts and thus an inhomogeneity in, for example, the catalyst activity over the reactor.

For example, it is possible for the reaction of hydroperoxide with propene to form products which are able to react further either with hydroperoxide or propene or both with hydroperoxide and propene to form an undesirable downstream product. In this case, the concentration of desired product and thus the probability of undesirable downstream product being formed becomes ever greater as the reaction mixture passes through the reactor. Accordingly, it is possible, for example, to use a first zeolite catalyst in a first reactor zone and in a second reactor zone to use a different zeolite catalyst which still catalyzes the reaction of hydroperoxide and organic compound but is less reactive in respect of the further reaction to the undesirable downstream product than is the zeolite catalyst in the first reactor zone.

Preference is given, for example, to using a titanium zeolite catalyst of the crystal structure type Ti-MWW having a high titanium content and accordingly a high activity in respect of the reaction of propene with hydroperoxide in a first compartment of the reactor and a titanium zeolite catalyst of the crystal structure type Ti-MWW having a lower titanium content than the first titanium zeolite catalyst in a second compartment. In a likewise preferred embodiment, the two titanium zeolite catalysts have different crystal structures, for example a crystal structure of the MFI type in the case of the catalyst in the first compartment and a crystal structure of the MWW type in the case of the catalyst in the second compartment. It is likewise possible for the catalyst in the first compartment to have a crystal structure of the MWW type and the catalyst in the second compartment to have a crystal structure of the MFI type. In these embodiments, particular preference is given to the reaction mixture firstly passing through the first compartment and subsequently passing through the second compartment on its way through the reactor.

Accordingly, the present invention also describes a reactor for the reaction of propene with a hydroperoxide, comprising at least two physically separate, different zeolite catalysts of the crystal structure type MWW.

The compartmentalization according to the present invention can also be achieved, for example, by use of at least two reactors connected in series, with at least one zeolite catalyst being used for the reaction in a first reactor and at least one further zeolite catalyst which differs from the zeolite catalyst used in the first reactor being used for the reaction in at least one further reactor and at least one of the catalysts being a zeolite catalyst, preferably a titanium zeolite catalyst, of the crystal structure type MWW.

In this embodiment, it is possible, for example, to use a first catalyst in at least one first reactor and in at least one second reactor to use a second catalyst different from the first catalyst, with the catalyst in the first reactor being able to be, for example, in the form of zeolitic material or shaped bodies or a mixture of zeolitic material and shaped bodies and the catalyst in the second reactor being in the form of zeolitic material or shaped bodies or a mixture of zeolitic material and shaped bodies.

Likewise, the catalyst can, for example, be used as a mesh catalyst based on inert woven meshes such as inert woven meshes made of metals, plastics, aluminum oxides, glass fibers, carbon fibers and/or graphite. Based on the weight of zeolite catalyst, such mesh catalysts preferably have an alkali metal content of less than 500 ppm. These mesh catalysts are preferably produced by a process in which at least one zeolite, preferably at least one titanium zeolite, is crystallized onto an inert woven mesh. Mesh catalysts of this type and ways of producing them are described in EP 0 883 439 B1, whose relevant contents are fully incorporated by reference into the context of the present invention.

Accordingly, the present invention also describes an assembly of reactors connected in series for the reaction of propene with a hydroperoxide, which comprises it least two reactors and in which at least two reactors contain different zeolite catalysts.

As zeolite catalysts which are different from the zeolite catalyst of the crystal structure type MWW, specific mention may be made of titanium-, germanium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structures and to mixed structures derived from two or more of the abovementioned structures. It is also conceivable to use titanium-containing zeolites having the ITQ-4, SSZ-24, TTM-1, UTD-1, CIT-1 or CIT-5 structure in the process of the present invention. Further titanium-containing zeolites which may be mentioned are those of the ZSM-48 or ZSM-12 structure.

Details of these structure types may be found in the abovementioned reference W. M. Meier, D. H. Olson and Ch. Baerlocher "Atlas of Zeolite Structure Types", Elsevier, $5^{th}$ edition, pp. 202 and 203, Amsterdam 2001.

Titanium zeolites, in particular those having a crystal structure of the MFI type, and possible ways of preparing them are described, for example, in WO 98/55228, EP-A 0 311 983 or EP-A 0 405 978, whose relevant contents are fully incorporated into the disclosure of the present patent application.

In this assembly of reactors connected in series it is possible, for example, to carry out the reaction in the first reactor in the presence of a first catalyst of the TS-1 type and in the second reactor in the presence of a second catalyst of the MWW type. Preference is given, for example, to using methanol or a methanol/water mixture as solvent in the first reactor and at least one nitrile, preferably acetonitrile, or a nitrile/water mixture, preferably an acetonitrile/water mixture, as solvent in the second reactor. It is likewise possible to use the catalyst of the MWW type in the first reactor and the catalyst of the TS-1 type in the second reactor.

The following examples illustrate the invention.

EXAMPLES

Example 1a

Activity Test Using TS-1 in Methanol as Solvent

In a 2 l steel autoclave provided with a stirrer, 100 g of spray-dried, calcined, titanium zeolite (Ti content: 1.5% by weight) prepared according to the working example in DE-A 199 39 416, were stirred together with 108 g of ammonia solution (25% by weight) and 972 g of deionized water at 300 rpm and maintained at 125° for 24 hours.

After the reaction was complete, the contents of the reactor were filtered with suction and the solid was washed three times with a total of 1500 ml of deionized water.

The filter cake was dried in air at 120° C. for 4 hours and finally calcined in air at 550° C. for 3 hours.

The weight of the product was 93 g, and the material had a Ti content of 1.5% by weight.

In the catalytic activity test, 0.5 g of titanium zeolite TS-1 prepared as described above were introduced together with 45 ml of methanol into a glass pressure-proof reactor, and 20 ml of propene were introduced at 0° C. and 18 g of hydrogen peroxide (Merck, 30% by weight in water) were subsequently fed in by means of a pump. After a reaction time of 5 hours, the mixture was depressurized and the liquid phase was analyzed by gas chromatography. The reaction mixture contained 6.2% by weight of propylene oxide.

Example 1b

Activity Test Using TS-1 in Acetonitrile as Solvent

Example 1a was repeated with the catalytic activity test being carried out using acetonitrile instead of methanol as solvent.

The reaction mixture contained 1.1% by weight of propylene oxide.

Example 2a

Activity Test Using Ti-MWW in Acetonitrile as Solvent

The preparation was carried out as described in Example 1 of WO 02/28774. 112 g of Aerosil were used as silica source. The weight of Ti-MWW product was 70 g and the material had a Ti content of 4.6% by weight and displayed an X-ray diffraction pattern typical of Ti-MWW.

In a catalytic activity test, 0.5 g of titanium zeolite Ti-MWW was introduced together with 45 ml of acetonitrile into a glass pressure-proof reactor, and 20 ml of propene were introduced at 0° C. and 18 g of hydrogen peroxide (Merck, 30% by weight in water) were subsequently fed in by means of a pump. After a reaction time of 5 hours, the mixture was depressurized and the liquid phase was analyzed by gas chromatography. The reaction mixture contained 5.3% by weight of propylene oxide.

Example 2b

Activity Test Using Ti-MWW in Methanol as Solvent

Example 2a was repeated with the catalytic activity test being carried out using methanol instead of acetonitrile as solvent.

The reaction mixture contained 1.9% by weight of propylene oxide.

Example 3

35 g of the Ti-MWW powder prepared as described in Example 2a were mixed well with 45 g of silica sol (Ludox® AS 40, 40% by weight of silicon dioxide) and a total of 20 g of polystyrene dispersion (33.5% by weight in water) and also 1.5 g of methylcellulose (Walocel®) and 45 g of water in a kneader.

During kneading, the polystyrene dispersion was added continuously over a period of 1 minute and, after 3 minutes, 37.5 g of Ludox® were added slowly. After kneading for a further 2 minutes, 10 g of water were added and after a further 10 minutes another 15 g of water were added slowly. After a further 10 minutes, the remaining silica sol was added and the remaining water was subsequently added in portions over a period of 10 minutes. Methylcellulose was firstly mixed with the dried powder in the kneader.

After a total kneading time of 70 minutes, the resulting paste was extruded in a ram extruder under a pressure of 60 bar through a die having 1.5 mm holes to form extrudates.

The product obtained in this way was dried in air at a heating rate of 2° C./min to 120° C. for 4 hours. It was subsequently calcined in air at a heating rate of 1° C./min to 490° C. for 5 hours. The yield was 41 g.

The titanium content of the catalyst prepared in this way was 2.8% by weight and the pore volume determined by mercury porosimetry in accordance with DIN 66133 was 1.2 ml/g.

Example 4

15.1 g of the catalyst obtained as described in Example 3 were installed in a tube reactor having a length of 1.3 m and, at a pressure of 20 bar, 66 g/h of acetonitrile, 8.9 g/h of hydrogen peroxide (40% by weight) and 7 g/h of propene (96% by volume of propene) were passed over the catalyst at temperatures in the range from 30 to 60° C.

After continuous operation for 400 hours, analysis of the product mixture leaving the reactor indicated a mean selectivity to propylene oxide, based on hydrogen peroxide of 81.5% and a mean selectivity to epoxide downstream products, based on hydrogen peroxide, of 4.7%. The mean selectivity to glycol as epoxide downstream products was 1.4%. The selectivity in respect of oxygen was on average 13.8%.

Example 5

9 g of the catalyst from Example 3 were heated to 140° C. with 100 g of deionized water in an autoclave while stirring and stirred for a period of 36 hours. The mixture was subsequently cooled, the solid was filtered off, dried at 120° C. for 4 hours and calcined in air at 450° C. The weight of product was 8.8 g.

Example 6

8.8 g of the catalyst obtained in Example 5 were installed in a tube reactor (length: 1.3 m) and, at 20 bar, a feed of 42 g/h of acetonitrile, 5.5 g/h of hydrogen peroxide (40% by weight) and 4.5 g/h of propene (96% by volume of propene) was passed over the catalyst at temperatures in the range from 30 to 65° C.

After continuous operation for 325 hours, analysis of the product mixture leaving the reactor indicated a mean selectivity to propylene oxide, based on hydrogen peroxide, of 87.6% and a mean selectivity to epoxide downstream products, based on hydrogen peroxide, of 6.0%. The mean selectivity to glycol as epoxide downstream products was 1.6%. The selectivity in respect of oxygen was on average 6.5%.

We claim:
1. A shaped catalyst body, comprising:
   at least one porous oxidic material as catalytically active material,
   wherein the porous oxidic material is a titanium zeolite which is assigned X-ray-crystallographically to the MWW type, said shaped catalyst body being obtainable by a process comprising:
   (a) preparing the at least one porous oxidic material;
   (b) producing a shaped body using the porous oxidic material obtained in (a), by a process comprising:

(aa) kneading the porous oxidic material obtained in (a) with addition of a polystyrene dispersion as a pore former and optionally, at least one other pore former, and optionally at least one binder or at least one extrusion aid or a water-containing composition or a mixture of two or more thereof;

(bb) shaping the kneaded mixture obtained in (aa) or give at least one shaped body;

(cc) drying the shaped body obtained in (bb);

(dd) calcining the dried shaped body obtained in (cc).

2. A shaped catalyst body, comprising:

at least one porous oxidic material as catalytically active material, wherein the porous oxidic material is a titanium zeolite which is assigned X-ray-crystallographically to the MWW type, said shaped catalyst body being obtainable by a process comprising:

(a) preparing the at least one porous oxidic material;

(b) producing a shaped body using the porous oxidic material obtained in (a), by a process comprising:

(aa) kneading the porous oxidic material obtained in (a) with addition of at least one binder or at least one extrusion aid or at least one pore former or a water-containing composition or a mixture of two or more thereof;

(bb) shaping the kneaded mixture obtained in (aa) or give at least one shaped body;

(cc) drying the shaped body obtained in (bb);

(dd) calcining the dried shaped body obtained in (cc), wherein after any one of (bb), (cc), or (dd) the shaped body obtained in (bb) is brought into contact with a water-containing composition at a temperature of from 100 to 250° C.

3. The shaped catalyst body of claim 2, wherein the water-containing composition is water.

4. The shaped catalyst body of claim 2, wherein the contacting with a water-containing composition is conducted at a temperature ranging from 120 to 250° C.

5. The shaped catalyst body of claim 2, wherein the contacting lasts for a duration of from 12 to 48 h.

6. The shaped catalyst body of claim 2, wherein the contacting takes place in an autoclave.

7. The shaped catalyst body of claim 6, wherein when the shaped body is brought into contact with a water-containing composition after (cc) or (dd), said bringing into contact is followed by a further drying and/or calcination step.

8. The shaped catalyst body of claim 2, wherein in (aa) at least one pore former is added, said pore former being a polystyrene dispersion.

* * * * *